United States Patent [19]
Ambers

[11] 4,298,026
[45] Nov. 3, 1981

[54] SPOOL VALVE

[75] Inventor: Paul J. Ambers, Westwood, Mass.

[73] Assignee: Instrumentation Laboratory Inc., Lexington, Mass.

[21] Appl. No.: 104,296

[22] Filed: Dec. 17, 1979

[51] Int. Cl.³ .............................................. F16K 5/04
[52] U.S. Cl. .............................. 137/625.47; 137/265; 137/571; 422/63; 251/DIG. 1
[58] Field of Search ................... 137/625.47, 265, 571; 251/DIG. 1

[56] References Cited

U.S. PATENT DOCUMENTS

| | | |
|---|---|---|
| 1,228,469 | 6/1917 | Mueller . |
| 1,977,181 | 10/1934 | Foresman . |
| 2,337,321 | 12/1943 | Freeman ......................... 137/625.47 |
| 2,641,280 | 6/1953 | Fleischhauer . |
| 3,115,896 | 12/1963 | Roberts et al. . |
| 3,165,122 | 1/1965 | Sachnik ......................... 137/625.47 |
| 3,251,419 | 5/1966 | Howard ..................... 137/625.47 X |
| 3,618,637 | 11/1971 | Santomieri ................. 137/625.47 X |
| 3,692,041 | 9/1972 | Bondi . |
| 3,963,440 | 6/1976 | Stein et al. . |

FOREIGN PATENT DOCUMENTS

| | | | |
|---|---|---|---|
| 1161603 | 9/1958 | France ............................ 137/625.47 |
| 72375 | 11/1959 | France ............................ 137/625.47 |
| 1204393 | 1/1960 | France ............................ 137/625.47 |

Primary Examiner—Arnold Rosenthal

[57] ABSTRACT

A valve includes housing and body members that have cylindrical valve surfaces. The valve body being centered in the housing by an array of at least three resilient support elements circumferentially spaced about the valve body. The valve body includes a plurality of ports arranged for selective alignment with housing ports as the valve body member is rotated and a through passage that connects two of the valve body ports. The resilient support members are apertured and conform in sealing engagement between the juxtaposed cylindrical valve surfaces so that they also function as annular valve seal members.

10 Claims, 7 Drawing Figures

SPOOL VALVE

This invention relates to valve arrangements, and more particularly to valve arrangements that have particular application in precious fluid handling systems such as apparatus for the analysis of parameters of blood or the like.

The values of particular constituents of a previous fluid sample, such as blood, often are useful in providing diagnostic information or for the control of life support devices. For example, pH, $PCO_2$, and $PO_2$ values of blood specimens provide important clinical information and analysis systems employing electrochemical electrodes have been developed for such analyses.

In such analyses, it is frequently important to minimize the required volume of the fluid sample, and an object of this invention is to provide improved valve arrangements useful for such applications.

In one type of analysis system, a fluid sample is drawn through a common inlet and distributed to a plurality of analysis chambers. Such an arrangement provides convenient operation reduces sample handling, and facilitates proper coordination of several different parameter measurements on a single fluid sample. To maintain measurement accuracies, the individual electrochemical electrode systems are checked or calibrated periodically. Different calibration media are frequently used for different electrode systems, for example, in a blood analysis instrument of the type shown in Zindler et al. U.S. Pat. No. 3,960,498, the carbon dioxide and oxygen sensors are calibrated with two gas mixtures, each of which contains known amounts of oxygen and carbon dioxide, and the pH electrode system is calibrated with two different buffer liquids. Another object of this invention is to provide a novel and improved precious fluid analysis system.

In accordance with the invention there is provided a valve that has particular application in an electrochemical analysis system that includes a plurality of flow-through analysis chambers. In that system the valve is connected in series between the outlet port of one analysis chamber and the inlet port of a second analysis chamber. The valve includes a housing member that has a recess in which a valve body member is disposed. The housing and body members include coaxial cylindrical valve surfaces in juxtaposed spaced relation with the valve body being centered in the housing recess by an array of at least three resilient support elements circumferentially spaced about the valve body between the juxtaposed spaced valve surfaces. Means disposed in the annular space between the housing and body valve surface fixes the resilient support elements in predetermined circumferential and axial positions between the two valve surfaces. Formed in the housing member are a plurality of passages, each of which terminates in a port in the housing valve surface. The valve body includes a plurality of ports arranged for selective alignment with the housing ports as the valve body member is rotated relative to the valve housing member and a through passage in the valve body member connects two of the valve body ports. At least two of the resilient support members are apertured and the positioning means locates those apertured support elements in alignment with ports on one of the juxtaposed members. Each such apertured support member conforms in sealing engagement between the juxtaposed cylindrical valve surfaces and thus also functions as an annular valve seal member.

Preferably the through passage has a volume of less than fifteen microliters, and in a particular embodiment the through passage extends transversely along a diameter of the body member and has a volume of about three microliters. In that embodiment, the valve body has a plurality of axially extending passages, each of which extends from one end surface of the valve body to a radial passage that terminates in a port axially aligned with but radially offset from the ports of the through passage. The support element positioning means is an annular sleeve that is fixed to the housing member and all of the resilient support elements are toroidal synthetic rubber seal members, each seal member has a passage about one millimeter in diameter and is fixedly positioned by the annular sleeve. Collar structure at the open end of the housing recess journals the valve body for rotation within the housing between an analysis position (in which the through passage connects the analysis chambers) and calibrating positions. This valve embodiment is electrically inert and imposes no significant change in electrical influence on the electrochemical measuring systems between its sampling and calibration positions and enables multiple analyses of minute volumes of precious fluid samples in a resiliently supported and sealed arrangement which can be easily and thoroughly flushed and which is easily shiftable for alternate calibration and analysis modes as desired.

Other features and advantages of the invention will be seen as the following description of a particular embodiment progresses, in conjunction with the drawings in which.

Figure 5:
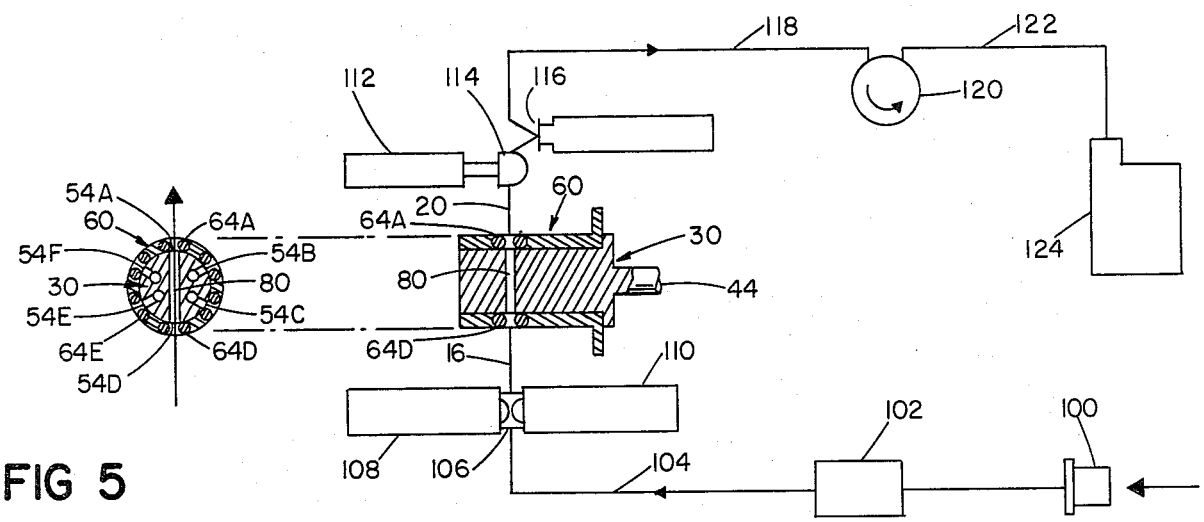
Figure 6:
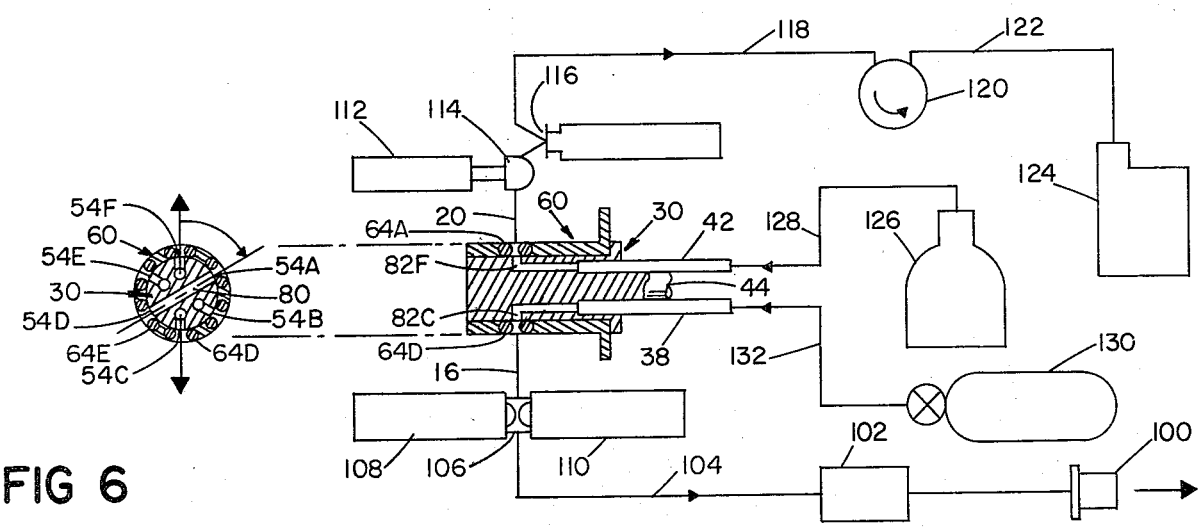
Figure 7:
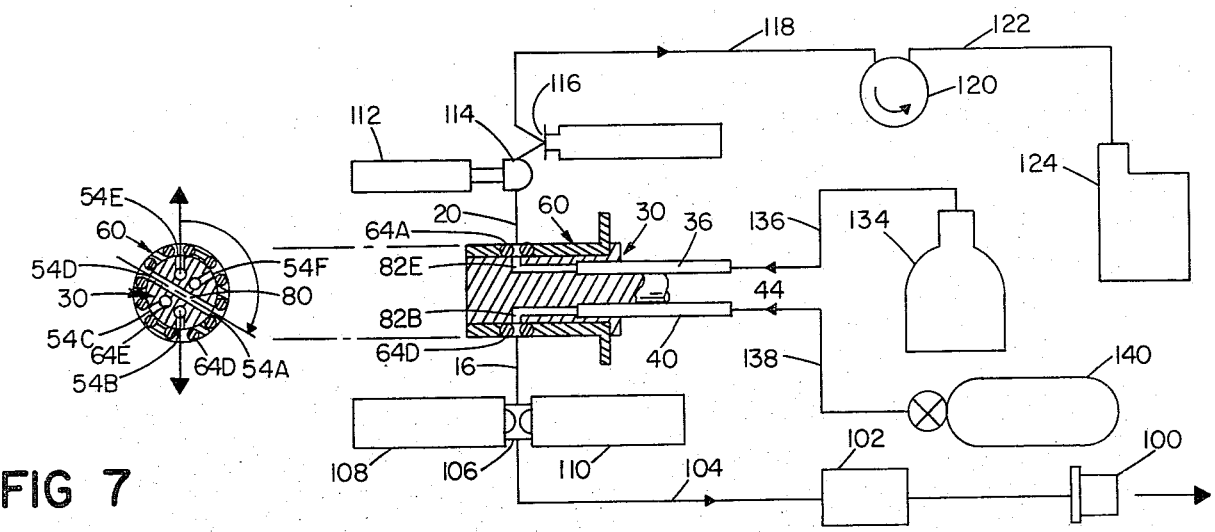

FIGS. 5, 6, and 7 are diagrammatic view of a precious fluid analysis system showing flow paths in three different valve positions.

DESCRIPTION OF PARTICULAR EMBODIMENT

Figure 1:
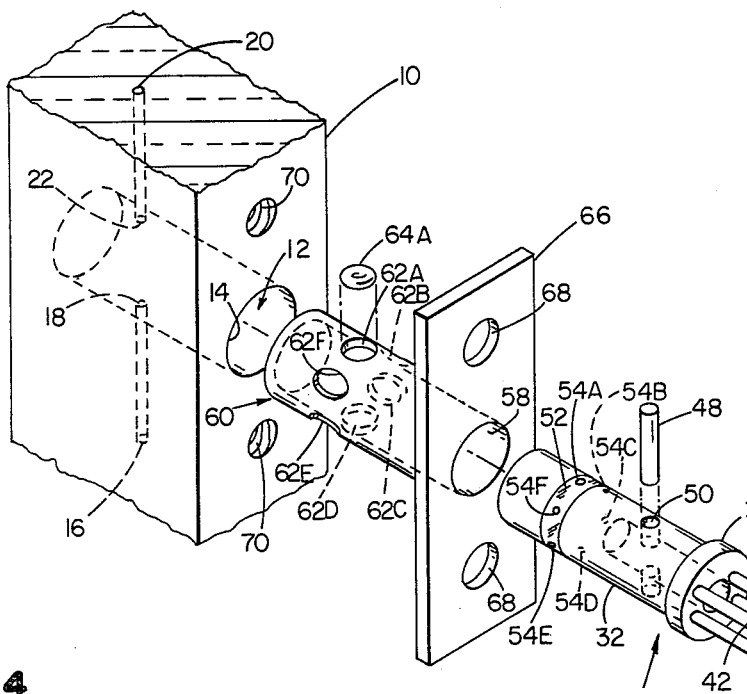
FIG. 1 is an exploded view of a valve arrangement in accordance with the invention.

The valve arrangement shown in the exploded view of FIG. 1 includes an acrylic housing member 10 in which is formed recess 12 that has cylindrical valve surface 14 of about one centimeter diameter. Inlet passage 16 (about 0.7 millimeter in diameter) extends from a first analysis chamber and terminates in port 18 in valve surface 14; and outlet passage 20 (also about 0.7 millimeter in diameter) extends radially outward from port 22 in valve surface 14 to a second analysis chamber.

Valve member 30 includes stainless steel cylindrical spool portion 32 that is about two centimeters long and about three-quarter centimeter in diameter; and collar member 34 secured to the outer end of spool 32. Tubes 36, 38, 40, and 42 extend axially from collar 34. Stub shaft 44 is secured in axially extending recess 46 by pin 48 that is received in transverse bore 50. Cylindrical valve surface 52 of body 32 has an 8 micro finish and formed therein are six ports 54, each of which has a smoothly curved entrance transition to a radially extending passage of about 0.7 millimeter diameter.

Cylindrical Delrin sleeve 60 (of about one millimeter wall thickness) is disposed in the annular space between valve surfaces 14 and 52. Sleeve 60 has a series of six apertures 62 arranged in a circumferential ring about sleeve 60. Disposed in each aperture 62 is a toroidal, synthetic rubber member 64 (of ninety durometer Viton rubber). Each member 64 has an outer diameter of about one-third centimeter, a cross-sectional diameter of about 1.2 millimeter, and an inner diameter of about one millimeter. Secured to sleeve 60 is flange 66, the holes 68 of which are aligned with threaded holes 70 in housing member 10.

Retainer plate 72 had cylindrical journal surface 74 which receives collar 34 and retaining flange portion 76. Bolts (not shown) pass through apertures 78 in retainer plate 72 and apertures 68 in sleeve flange 66 and are threaded into holes 70 to secure the valve assembly together.

Figure 2:
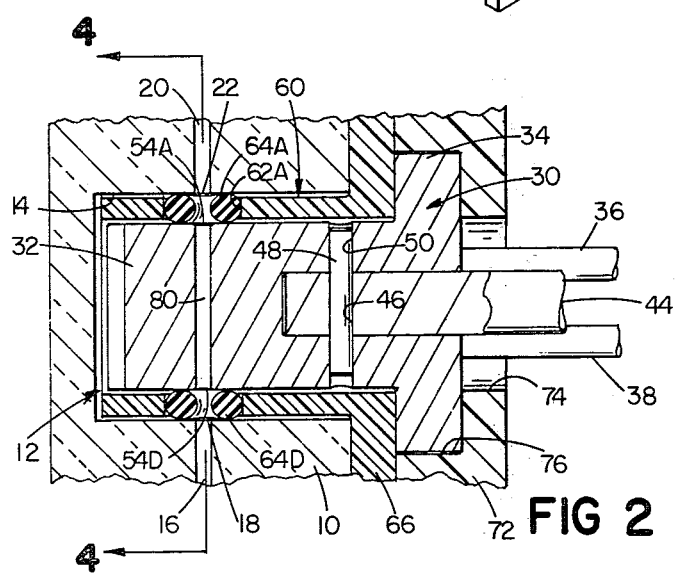
FIG. 2 is a longitudinal sectional view through the valve arrangement of FIG. 1.
Figure 3:
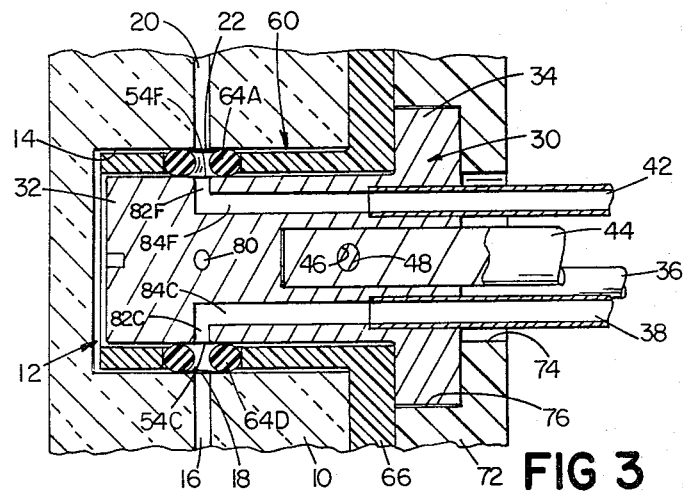
FIG. 3 is a longitudinal sectional view, similar to FIG. 2, showing the valve arrangement in a second position.
Figure 4:
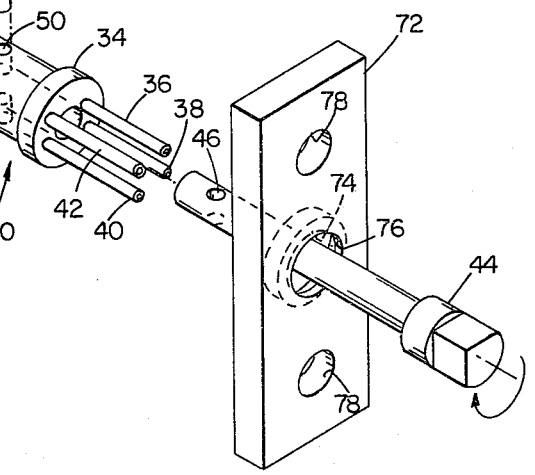
FIG. 4 is a transverse sectional view taken along the line 4—4 of FIG. 2.

Further details of the valve assembly may be seen with reference to the sectional views of FIGS. 2, 3, and 4. Through passage 80 (0.7 millimeter in diameter) extends through valve body 32 between ports 54A and 54D. Extending radially inward from each port 54B, 54C, 54E, and 54F is a 0.7 millimeter diameter passage 82 that intersects with a one millimeter diameter axially extending passage 84 which in turn is connected to tubes 36, 38, 40, and 42 respectively. The edge of each port 54 is smoothly rounded (at about 0.2 millimeter radius). Each toroidal member 64, as indicated in FIG. 4, is disposed between and circumferentially conforms to cylindrical valve surfaces 14 and 52 to provide a sealing region surrounding each port 54. The circumferentially extending array of members 64 provide resilient centering support for spool 32 within recess 12.

A blood gas analysis system that incorporates the valve shown in FIGS. 1–4 is diagrammatically shown in FIGS. 5, 6, and 7. The blood gas analysis system includes an inlet 100 through which a blood sample is introduced into the system. Inlet 100 is connected to heater 102 which is connected by conduit 104 to analysis chamber 106. Disposed in communication with chamber 106 is a $PO_2$ electrode 108 and a $PCO_2$ electrode 110. The outlet of chamber 106 is connected by passage 16 to valve housing port 18. Valve housing port 22 is connected by passage 20 to capillary measuring chamber 114 of pH electrode 112 and reference junction structure 116. The reference junction is in turn connected by conduit 118 through peristaltic pump 120 and conduit 12 to waste receptacle 124.

In the analysis position shown in FIG. 5, valve spool 32 is positioned so that through passage 80 provides communication between passages 16 and 20. In a first calibrating position (shown in FIG. 6), the valve spool is rotated sixty degrees so that port 54F is aligned with housing passage 20 and port 54C is aligned with housing passage 16; connecting buffer liquid container 126 to pH electrode 112 via conduit 128 tube 62 and passage 22; and connecting gas bottle 130 via conduit 132, tube 58 and passage 16 to gas cuvette 106. In the third position of the valve spool (shown in FIG. 7), port 54E is aligned with passage 20 (connecting buffer liquid container 134 to pH electrode 112 via conduit 136, tube 56, and passage 20) and port 54B is aligned with passage 16 (connecting calibrating gas container 140 to chamber 106 via conduit 138, tube 60 and passage 16). Resilient support elements 64 slide on spool surface 52 as the spool 30 is rotated.

In an analysis operation, with the valve in the position shown in FIG. 5, a blood sample of about sixty-five microliters volume is introduced into measuring chambers 106, 114, 116 by operation of peristaltic pump 120. That sample volume is first placed in preheater 102, and then that heated sample volume is moved from preheater 102 to analysis chambers 106 and 114 and reference junction 116 with the sample volume extending through the three microliter volume passage 80 of the valve. pH, $PO_2$, and $PCO_2$ measurements on that microsample are made simultaneously be electrodes 108, 110, and 112.

In preparation for such an analysis, the oxygen and carbon dioxide sensors 108, 110, are calibrated with two gases from sources 130, 140; and pH sensor 112 is calibrated with buffer liquids from sources 126 and 134. With the valve in the analysis position (FIG. 5) and with inlet 100 immersed in flush solution, peristaltic pump 120 is operated to draw flush solution through the system in a cleaning operation. Valve spool 30 is then rotated 60 degrees to a first calibration position (FIG. 6) in which cuvette 106 is connected to gas source 130 and pH measuring chamber 114 is connected to high buffer source 126. In this valve position, the gas flowing through cuvette 106 has a mixture of about five percent carbon dioxide, twelve percent oxygen, and the balance nitrogen. Peristaltic pump 120 is operated to place high buffer liquid in chamber 114 and at reference interface 116. The carbon dioxide, oxygen and pH electrode translating circuitries, are adjusted in zeroing operations. The valve spool is then rotated 60 degrees to the third position (FIG. 7) in which a gas (about ten percent carbon dioxide, no oxygen, and the remainder nitrogen) from source 140 is applied to cuvette 106 and in the low buffer source 134 is connected to pH measuring chamber 114. Peristaltic pump 120 is operated to place the low buffer liquid in chamber 114 and at reference interface 116. The oxygen, carbon dioxide and pH electrodes are then further adjusted in a second calibration step.

When the response of the electrode systems have been satisfactorily calibrated, the valve spool is rotated to the analysis position (FIG. 5) and the instrument is ready for analysis sequence. Sample inlet 100 is removed from the flush solution and a sixty-five microliter blood sample is inducted into preheater 102. After the sample is heated, it is flowed into measuring chambers 106 and 114 and past liquid junction 116, and measurements of pH, $PCO_2$, and $PO_2$ are simultaneously obtained on the sample. After the measurements are complete, the sample is flushed from the analysis chambers 106 and 114 by operation of pump 120, and flush solution is drawn through the system in a cleaning operation. Calibration of the electrode systems may be periodically checked by placing the valve in a calibrate position and allowing the selected calibrated gas to flow through chamber 106 and pumping the selected buffer liquid through chamber 114. As the valve spool is moved from the analysis position to a calibrate position flush solution is vented from passage 80 to the juxtaposed valve surfaces of the valve in a self-lubricating action.

While a particular embodiment of the invention has been shown and described, it is not intended that the invention be limited to the disclosed embodiment or to details thereof and departures may be made therefrom within the spirit and scope of the invention.

What is claimed is:

1. A valve comprising a housing member that has a recess, a body member disposed in said recess, said housing and body members including coaxial cylindrical valve surfaces in juxtaposed spaced relation, an array of at least three resilient support elements circumferentially spaced about said valve body between said juxtaposed spaced valve surfaces for centering said valve body in said housing recess, positioning means in said annular space between said housing and body valve surfaces fixing said resilient support elements in predetermined circumferential and axial positions between said two valve surfaces, a plurality of passages in said housing member, each said housing passage terminating in a port in said housing valve surface, a plurality of ports in said valve surface of said valve body arranged for selective alignment with said housing ports as said valve body member is rotated relative to said valve housing member, a plurality of separate passages in said valve body including a through passage connecting two of said valve body ports and a second passage separate from said through passage connecting a third of said valve body ports to a fourth port in said valve body, at least two of the resilient support elements being apertured and said positioning means locating said apertured support elements in alignment with ports on one of the juxtaposed members such that each said apertured support element conforms in sealing engagement between said juxtaposed cylindrical valve surfaces and functions as an annular valve seal member, said valve body being mounted for movement within said housing member between a first position in which said through passage connects first and second passages in said housing member and a second position in which said second body passage connects one of said ports in said housing member to said fourth port in said valve body member.

2. A precious fluid analysis system comprising a plurality of flow-through analysis chambers, a valve connected in series between the outlet port of one analysis chamber and the inlet port of a second analysis chamber, said valve comprising a housing member that has a recess, a body member disposed in said recess, said housing and body members including coaxial cylindrical valve surfaces in juxtaposed spaced relation, an array of at least three resilient support elements circumferentially spaced about said valve body between said juxtaposed spaced valve surfaces for centering said valve body in said housing recess, positioning means in said annular space between said housing and body valve surfaces fixing said resilient support elements in predetermined circumferential and axial positions between said two valve surfaces, a plurality of passages in said housing member, each said housing passage terminating in a port in said housing surface, a plurality of ports in said valve surface of said valve body arranged for selective alignment with said housing ports as said valve body member is rotated relative to said valve housing member, a plurality of separate passages in said valve body including a through passage connecting two of said valve body ports and a second passage separate from said through passage connecting a third of said valve body ports to a fourth port in said valve body, at least two of the resilient support elements being apertured and said positioning means locating said apertured support elements in alignment with ports on one of the juxtaposed members such that each said apertured support element conforms in sealing engagement between said juxtaposed cylindrical valve surfaces and functions as an annular valve seal member, said valve body being mounted for rotation within said housing between an analysis position in which said through passage connects said first and second analysis chambers and a second position in which said second passage connects one of said ports in said housing member to said fourth port in said valve member.

3. The valve of claim 1 or 2 wherein said through passage extends transversely along a diameter of said body member, is of uniform cross-section along its length, and has a volume of less than fifteen microliters.

4. The valve of claim 3 wherein each of said resilient support elements is a toroidal synthetic rubber seal member.

5. The valve of claim 3 wherein said support element positioning means is an annular sleeve that is fixed to said housing member.

6. A precious fluid analysis system comprising a plurality of flow-through analysis chambers, a valve connected in series between the outlet port of one analysis chamber and the inlet port of a second analysis chamber, said valve comprising a housing member that has a recess, a body member disposed in said recess, said housing and body members including coaxial cylindrical valve surfaces in juxtaposed spaced relation, an array of at least three resilient support elements circumferentially spaced about said valve body between said juxtaposed spaced valve surfaces for centering said valve body in said housing recess, positioning means in said annular space between said housing and body valve surfaces fixing said resilient support elements in predetermined circumferential and axial positions between said two valve surfaces, a plurality of passages in said housing member, each said housing passage terminating in a port in said housing valve surface, a plurality of ports in said valve surface of said valve body arranged for selective alignment with said housing ports as said valve body member is rotated relative to said valve housing member, a plurality of separate passages in said valve body including a through passage connecting two of said valve body ports and a plurality of axially extending passages, each said axially extending passage extending from one end surface of said valve body to a radial passage that terminates in a port circumferentially aligned with but radially offset from the ports of said through passage, at least two of the resilient support elements being apertured and said positioning means locating said apertured support elements in alignment with ports on one of the juxtaposed members such that each said apertured support element conforms in sealing engagement between said juxtaposed cylindrical valve surfaces and functions as an annular valve seal member, said valve body being mounted for rotation within said housing between an analysis position in which said through passage connects said first and second analysis chambers and a second position in which at least one of said axially extending passages is connected to one of said ports in said housing member.

7. A valve comprising a housing member that has a recess, a body member disposed in said recess, said housing and body members including coaxial valve surfaces in juxtaposed spaced relation, an array of at least three resilient support elements circumferentially spaced about said valve body between said juxtaposed spaced valve surfaces for centering said valve body in said housing recess, positioning means in said annular space between said housing and body valve surfaces fixing said resilient support elements in predetermined circumferential and axial positions between said two valve surfaces, a plurality of passages in said housing member, each said housing passage terminating in a port in said housing valve surface, a plurality of ports in said valve surface of said valve body arranged for selective alignment with said housing ports as said valve body member is moved relative to said valve housing member, a plurality of separate passages in said valve body including a through passage connecting two of said valve body ports and an axially extending passage that extends from one end surface of said valve body to a radial passage that terminates in a third port in the valve surface of said body member, said third port being circumferentially aligned with but radially offset from the ports of said through passage, at least two of the resilient support elements being apertured and said positioning means locating said apertured support elements in alignment with ports on one of the juxtaposed members such that each said apertured support element conforms in sealing engagement between said juxtaposed cylindrical valve surfaces and functions as an annular valve seal member, said valve body being mounted for movement within said housing member between a first and second passages in said housing member and a second position in which a valve housing port is connected to said axially extending passage.

8. The valve of claim 6 or 7 wherein said through passage extends transversely along a diameter of said body member, is of uniform cross-section along its length, and has a volume of about three microliters.

9. The valve of claim 8 wherein each of said resilient support elements is a toroidal synthetic rubber seal member, each seal member having a passage about one millimeter in diameter and being fixedly positioned by said annular sleeve.

10. The valve of claim 9 wherein said valve surface of said valve body has a surface finish of at least sixteen microinches quality.

* * * * *